(12) United States Patent
Koo et al.

(10) Patent No.: US 6,736,000 B2
(45) Date of Patent: May 18, 2004

(54) STABLE GLOW DISCHARGE DETECTOR

(75) Inventors: Jackson C. Koo, San Ramon, CA (US); Conrad M. Yu, Antioch, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/919,171

(22) Filed: Nov. 15, 2001

(65) Prior Publication Data

US 2002/0029611 A1 Mar. 14, 2002

Related U.S. Application Data

(63) Continuation-in-part of application No. 09/464,668, filed on Dec. 15, 1999, now Pat. No. 6,457,347.

(51) Int. Cl.⁷ .......................... G01N 30/02; H01J 17/00
(52) U.S. Cl. .................. 73/23.4; 73/23.35; 73/31.03; 73/31.05; 422/89
(58) Field of Search .................. 73/23.4, 23.35, 73/31.03, 31.05; 422/89

(56) References Cited

U.S. PATENT DOCUMENTS 3,478,205 A * 11/1969 Sporek ..................... 73/23.35
3,656,339 A * 4/1972 Narain ..................... 73/23.35
5,955,886 A * 9/1999 Cohen et al. ............... 73/23.4
6,012,326 A * 1/2000 Raybone et al. ........... 73/31.03

OTHER PUBLICATIONS

Dai, P. et al., "A Novel High Sensitivity Micro GC Detector", Transducers '99, Jun. 7–10, 1999, pp. 696–699.*
Koo, J.C. et al., "Glow Discharge Detector", Jun. 7, 1999, p. 1–15.*

* cited by examiner

Primary Examiner—Daniel S. Larkin
(74) Attorney, Agent, or Firm—James S. Tak; Alan H. Thompson; Eddie E. Scott

(57) ABSTRACT

A highly sensitive electronic ion cell for the measurement of trace elements in He carrier gas which involves glow discharge. A constant wave (CW) stable glow discharge detector which is controlled through a biased resistor, can detect the change of electron density caused by impurities in the He carrier gas by many orders of magnitude larger than that caused by direct ionization or electron capture. The stable glow discharge detector utilizes a floating pseudo-electrode to form a probe in or near the plasma and a solid rod electrode. By using this probe, the large variation of electron density due to trace amounts of impurities can be directly measured. The solid rod electrode provides greater stability and thus easier alignment.

20 Claims, 2 Drawing Sheets

STABLE GLOW DISCHARGE DETECTOR

RELATED APPLICATION this application is a Continuation-In-Part of U.S. application Ser. No. 09/464,668 filed Dec. 15, 1999, now U.S. Pat. No. 6,457,347, issued Oct. 1, 2002, and entitled "Glow Discharge Detector."

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to the measurement of trace elements in a gas, particularly to the measurement of trace elements in He carrier gas of a hand-held gas chromatograph, and more particularly to a more stable glow discharge detector using a floating pseudo-electrode for measuring trace elements of the He carrier gas, the more stable glow discharge being controlled through a biased resistor, and thus constitutes an improvement over the glow discharge detector of above reference application Ser. No. 09/464,668, now U.S. Pat. No. 6,457,347.

In recent years, efforts have been directed to the development of a hand-held (portable) gas chromatograph. In a separation column of a gas chromatograph, chemical trace elements are carried by a carrier gas and each separated into small gas plugs through interaction with a coating inside the column. There has been a need for a highly sensitive detector for the detection of these trace chemical elements in these small gas plugs passing through the column for a gas chromatograph (GC). Among all conventional detectors used in the commercial GC systems, ion cell detectors seem to be physically most suitable for a portable GC system. However, in these conventional ion cell detectors, electrons and ions are generated by means of radioactive elements. Radioactive elements are hazardous and not suitable for general applications.

In normal ion cells, ions are generated by either radioactive isotopes, such as nickel 63, or pulsed arc sources. The percentage of ions of the trace elements generated is dependent upon their operational modes. In an electron capture mode of operation, almost all the trace element molecules are ionized by capturing electrons. However, the mode of operation is limited to the cases where trace element molecules have electron negativity. In an ionization mode of operation, only a small portion of trace element molecules are ionized. The total amount of trace element ions is certainly dependent upon the available sample volume. In a portable GC, the available sample volume is generally quite small, on the order of micro-liters. For low concentration trace elements, the signal generated through direct electron measurement is quite small and may well be below the sensitivity of existing electron instruments. Except for more costly optical detection methods, all the prior ion cells are not applicable to small sample size in the portable GC for general applications.

Recent progress in micro-machining technology has enabled the development of miniaturized gas chromatography (GC) systems with micromachined fluidics and detectors, as exemplified by U.S. Pat. No. 5,583,281 issued Dec. 10, 1996 to C. M Yu. However, the sensitivity of these early micro GC systems was well below that of conventional systems due to limitations of the micro thermal conductivity detectors (TCD) used in most of the micro GS systems.

Thus, efforts were directed to the development of a highly sensitive micro GC detector, which could replace the TCD in most portable GC systems and which has a potential to outperform some conventional GC detectors, such as the commonly used flame ionization detector (FID), nitrogen-phosphorous detector (NPD), and electron capture detector (ECD). These prior conventionally used high performance GC detectors are also sophisticated, heavy, large and require either make-up and detector gases and/or radioactive materials to operate, and they are not suitable for field applications where portability is a top priority.

A TCD, on the other hand, employs thermal conductivity differences in various gas species to sense the change in gas composition. Although a TCD lacks sensitivity when compared with a FID, NPD and ECD, it is a much simpler detector and is much easier to be adapted for field use. Such are exemplified in U.S. Pat. No. 5,591,896 issued Jan. 7, 1997, to C. Lin, and in P. Dai et al, A Novel High Sensitivity Micro GC Detector, Transducers 99, Jun. 7–10, 1999, pp. 696–699, Sandal, Japan. These sensors have two electrodes mounted along a single axis on a base substrate, and the two electrodes are separated by a narrow gap. One of the electrodes is tapered into a fine apex to create a strong concentration of electric field around the apex. When electric potential imposed upon the electrodes is sufficiently high, the gas molecules around the apex will be ionized. The ions and electrons generated by the ionization create an electric current flowing between the two electrodes across the gap. The electric current changes when gas composition changes because different gas molecules have different molecular structure and consequently different ionization characteristics, and this change is used as the micro detector's sensing signal. Polarity of the micro sensor can be set with the tapered electrode as either a cathode or an anode. These detectors measure the ionization properties of the sample gas in the glow discharge.

Recently, Hewlett Packard has developed a "Capillary Electron Capture Detector (ECD)" which also utilizes a pair of electrodes, one being tapered and one being hollow. This detector measures the effect of electron capture by means of sample gas molecules.

In a portable GC, an ion cell has to be non-radioactive, low power, low noise, and low cost, but rigid with high detection sensitivity.

The present invention provides a solution to the above-mentioned problem by providing a highly sensitive electronic ion cell which utilizes direct current (DC) glow discharge for the measurement of trace elements, in a carrier gas, such as He. The more stable glow discharge detector of this invention, like that of application Ser. No. 09/464,668, now U.S. Pat. No. 6,457,347, involves a constant wave (CW) direct current glow discharge controlled through a biased resistor. The glow discharge detector utilizes an extra floating pseudo-electrode to form a capacitor at the cathode dark space to detect the trace elements. The voltage drop between the cathode and the pseudo-electrode varies due to trace amounts of chemical components.

SUMMARY OF THE INVENTION

It is an object of the present invention to provide a means for measuring trace elements in a carrier gas.

A further object of the invention is to provide a more stable glow discharge detector for measuring variations of electron density due to trace amounts of chemical components in a carrier gas.

Another object of the invention is to provide a more stable glow discharge detector for measuring trace elements in an He carrier gas of a gas chromatograph.

Another object of the invention is to provide a direct current, constant wave glow discharge detector.

Another object of the invention is to provide an improved glow discharge detector controlled through a biased resistor and provided with a floating pseudo-electrode forming a probe.

Other objects and advantages of the present invention will become apparent from the following description and accompanying drawings. The present invention involves a more stable or improved glow discharge detector and like that of application Ser. No. 09/464,668, now U.S. Pat. No. 6,457,347, is particularly applicable for the measurement of trace elements in He carrier gas of a portable (hand-held) gas chromatograph. The stable glow discharge detector is of a direct current (DC), constant wave (CW) type and utilizes a floating pseudo-electrode to form a probe in the plasma. The probe enables direct measurement of the large variation of cathode drop voltage due to trace amounts of chemical components in the He carrier gas, which is many orders of magnitude larger than that caused by direct ionization or electron capture. Objects and advantages of the present invention will become apparent from the following description and accompanying drawings. The present invention involves a more stable or improved glow discharge detector and like that of application Ser. No. 09/464,668, now U.S. Pat. No. 6,457,347, is particularly applicable for the measurement of trace elements in He carrier gas of a portable (hand-held) gas chromatograph. The stable glow discharge detector is of a direct current (DC), constant wave (CW) type and utilizes a floating pseudo-electrode to form a probe in the plasma. The probe enables direct measurement of the large variation of cathode drop voltage due to trace amounts of chemical components in the He carrier gas, which is many orders of magnitude larger than that caused by direct ionization or electron capture.

BRIEF DESCRIPTION OF THE DRAWINGS

The accompanying drawings, which are incorporated into and form a part of the disclosure, illustrate an embodiment of the detector of application Ser. No. 09/468,668, now U.S. Pat. No. 6,457,347, and on embodiment of the invention and, together with the description, serve to explain the principles of the invention.

DETAILED DESCRIPTION OF THE INVENTION

Figure 1:
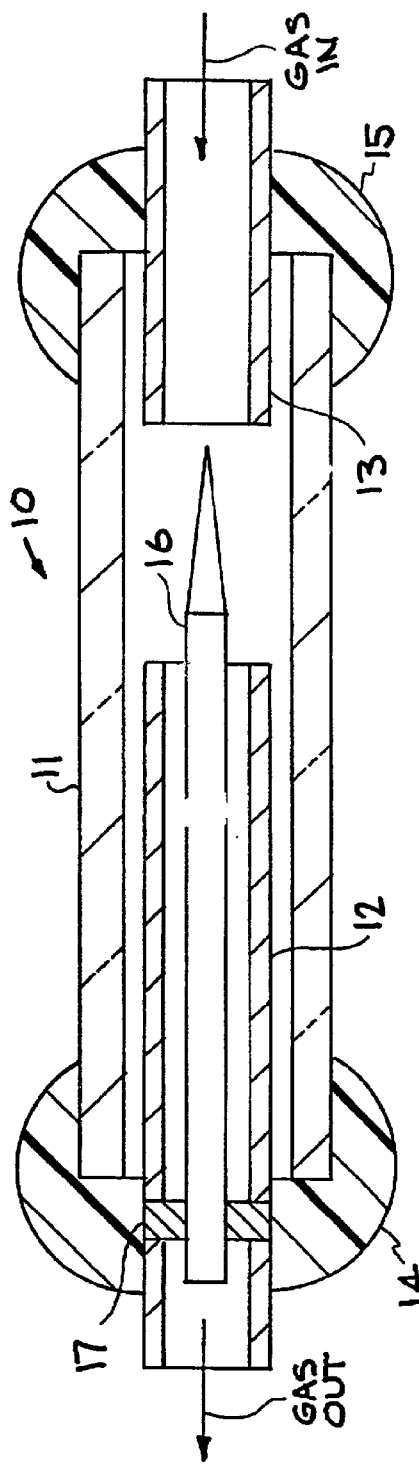
FIG. 1 is a partial cross-sectional view of an embodiment of a glow discharge detector of application Ser. No. 09/464,668, now U.S. Pat. No. 6,457,347.

The present invention, like that of application Ser. No. 09/464,668, now U.S. Pat. No. 6,457,347, involves a highly sensitive electronic ion cell for the measurement of trace elements in a carrier gas, such as He, in a gas chromatograph (GC) which utilizes a direct current (DC), constant wave (CW) glow discharge controlled through a biased resistor. In the resistor controlled CW glow discharge, the change of electron density caused by chemical components in the He carrier gas is many orders of magnitude larger than that caused by direct ionization or electron capture. To directly measure the electron density in the plasma of a glow discharge an extra floating pseudo-electrode has been added to form a probe in the plasma. By using this probe, chemical components can be directly measured.

In one liter of gas, there are about $10^{22}$ molecules. For a gas flow rate of one milliliter per second, there will be $10^{19}$ molecules per second flow through the detector. For a sample concentration of one part per million, there will be $10^{13}$ sample molecules per second flow through the system. In the electron capture process, sample molecules must have a high electronic affinity and each sample molecule will capture one electron. Therefore, there can be a modification of a total of about one micron ampere in the electronic circuit of the glow discharge system under this condition. The current in a glow discharge normally is in the order of one milli-ampere. In other words, there should be about 0.1% modification of the total current in a glow discharge. If the bias resistance is one meg-ohm, the signal voltage can be in the order of volts.

The ionization process in the glow discharge is quite weak, it is in the order of $10^{-4}$ to $10^{-5}$. In other words, the sample signal under the above situation will be in the order of 10 to 100 micro-volts. The gas flow rate of the GC of the present invention is only in the order of 10 to 100 micro-liters. The signal voltage will be 10 to 100 times smaller under the similar conditions. This means that the above-reference prior known detectors cannot be utilized for a portable GC.

Since in a small, portable (hand-held) GC, the sample sizes are micro-liters, and the normal commercial ion cells are both too big and are too low in sensitivity for the detection of the carrier gas chemical components. Also, as pointed out above, in a portable GC the ion cell has to be non-radioactive, low power, low noise, and low cost, but rigid with high detection sensitivity. Thus, one is limited to using low power, CW glow discharge for the detection of the trace elements. In a CW glow discharge controlled through a biased resistor, the change of cathode drop voltage caused by chemical components in the He carrier gas is many orders of magnitude larger than that caused by direct ionization or electron capture.

A DC glow discharge can be visualized as follows: By applying a voltage between a piece of positive metal plate (anode) and a sharp negative metal pin (cathode), an electrical field will exist between them. If the voltage is high enough, electrons start being pulled out off the sharp metal pin. This phenomenon is known as "field emission." If the electrons have enough energy, they start to ionize nearby molecules. Positive ions of these molecules are pulled back to the tip of the negative metal pin due to the electrical field to form a positive barrier and an extremely high electrical field region around the tip of the negative metal pin. This high electrical field causes further increasing of the emission of the electrons. Electrical current will continuously increase in the electrical circuit. The system continues to increase until it produces an avalanche breakdown. By inserting a resistor in the electrical circuit, this avalanche breakdown can be stopped. At that time, the external voltage between the anode and cathode becomes more or less a constant depending upon the surrounding gas. The electrical current is determined by the resistor used. This latter phenomenon is known as "dc glow discharge." The extremely high electrical field region between the positive ion barrier and the metal pin is called cathode dark space, because in this region there is no electron-ion recombination and no light emitted. In a normal glow discharge, there are several layers of dark spaces. The space between the positive barrier and the positive metal plate or anode is the region where bulk plasma exists. Because of recombination of a large number of ions and electrons in this region, this region is quite bright, which is referred to as "glow discharge."

In a glow discharge, voltage drop across the unit is mainly concentrated at the cathode dark space between the positive ion cloud and the emission point. There is a large electrolytic capacitance across this cathode dark space. Under the same ambient conditions, this voltage drop depends only on the compositions of the gases around the dark space. The electrical field produced by this cathode drop voltage at the cathode determines the electrical current flowing through the unit. Helium has the smallest nuclei, but the highest ionization potential. In a helium gas, under ambient condition, the value of this voltage drop becomes smallest. It is in the order of 400 volts. In the other gases, this voltage drop is in the order of 800 to 1200 volts. In the glow discharge detector of the present invention, this effect is used to detect sample gases.

As pointed out above, in a separation column of a GC, chemical trace elements are carried by a carrier gas and each separated into small gas plugs through interaction with the coating inside the column. As each plug of the trace chemical elements enters a glow discharge detector, because the molecules of these trace elements are different from those of the carrier gas in their electron affinity, molecules cross section and ionization potential, in first analysis, they certainly will cause the charge density in the bulk plasma of the glow discharge to vary. However, the charge density of a glow discharge is determined by external limitation. Any modification of the charge density in the bulk plasma by the trace elements must be instantaneously compensated by the internal field in the glow discharge detector (GDD). Variation of cathode drop voltage due to electrical current is logarithmically proportional to current.

For a GDD with a fixed structure and a particular carrier gas, its operational state is described solely by its operational voltage. The bias voltage and the resistor are external elements to the GDD and used only to determine the electrical current. For a fixed size plug of trace elements, it has a fixed time duration for passing the region of the GDD. The rise time of the signal is in the same order of magnitude as the passing duration of the trace element. The signal size of the trace elements will depend upon the rise time of the signal.

The high electrical field region in the dark space of the GDD is caused by positive ions of the carrier gas. These positive ions not only form a dark space, but also form a pseudo-electrode of one of a large capacitor. Any variation in the density of these positive ions or the distance between the positive ions to the cathode will cause the capacitor to charge or discharge through the external resistor. The rise time of a capacitor through a resistor is well known. It is equal to their product, CR. In this case, one can derive the capacitance from the data of constant current by assuming a value for the maximum signal. From the data of constant resistance, one can derive the relationship between the capacitance and the operational current. This shows approximately a linear relationship, or $$C=C(O)(1+\text{alpha}*I),$$

where alpha is a constant. In the case of hexane, it is measured to be 2.6 micro-farad per milli-ampere.

A preferred model for the detection by the GDD is as follows: As trace elements enter the space of bulk plasma region of a GDD, the effect of molecules interaction with charge particles is quickly compensated by the capacitance of its dark space. However, as the molecules of trace elements effect the electrical field strength in the dark space, the potential across the dark space will be forced to change. This change of the potential causes the capacitance in the dark space to discharge or charge up to the new potential through the external resistor in the external circuit with a rise time of CR. This is the source of signal in the GDD.

Since the dark space in a GDD is quite small, one can use the parallel plate structure in representing its capacitor. By assuming the area that glows on the top of the pin is the area of the capacitor, one can calculate its separation, the dark space of the glow discharge. At normal operation, the separation distance calculated is in the order of ten angstroms, the order of separation between molecules in ambient conditions. Different molecules will modify the internal potential and the capacitance due to their polarizability and their molecular size. Since helium has the smallest molecules and very low polarizability, at low concentration, molecules of trace elements cause a decrease of the capacitance in the dark space. To maintain a more or less constant value for the operational current, the potential across the dark space will have to increase. The potential across the resistor is equal to the difference between the external potential provided by power supply and more or less the potential across the dark space. This potential on the resistor will have to decrease. A negative signal will be measured. As the percentage trace molecules increases, some of the molecules of the trace element starts to be ionized by the emitted electrons from the cathode, and may form an additional positive barrier in the dark space. This will cause the increase of the capacitance and the potential in the dark space will decrease. One will measure a positive signal. As the percentage of the trace element increases again, the positive ions from the trace elements start to replace the positive ions of helium in the positive barrier, the signal can turn to negative again. The glow discharge may become unstable. It oscillates between two breakdown potentials.

The preferred mode of glow discharge can be used to explain the phenomena observed as the results of experiments carried out to verify the invention. In other words, the trace molecules detected through the GDD can be quite general as long as they are different from the carrier gas. Tests have shown that the GDD is quite sensitive in measuring PPB trace chemicals. The experimental testing is described in an article entitled, "Glow Discharge Detector," J. C. Koo et al., Lawrence Livermore National Laboratory, June 7, 1999.

Referring now to the drawings, FIG. 1 illustrates partial cross-section, the glow discharge detector made in accordance with above-referenced application Ser. No. 09/464,668, now U.S. Pat. No. 6,457,347. As shown, the detector, generally indicated at 10, comprises a glass tube 11 in which a pair of stainless steel or tungsten tubes 12 and 13 are coaxially mounted by a sealout, such as epoxy, indicated at 14 and 15. A tungsten member or pin 16 having a tapering end is coaxially mounted in stainless steel or tungsten tube 12 by the tube 12 being pinched as indicated at area 17, but such as to provide minimal blockage of gas flow through the detector. Glass tube 11 is mounted to a separation column of a GC whereby gas in the column passes therethrough as indicated by the gas in arrow and gas out arrow.

Figure 2:
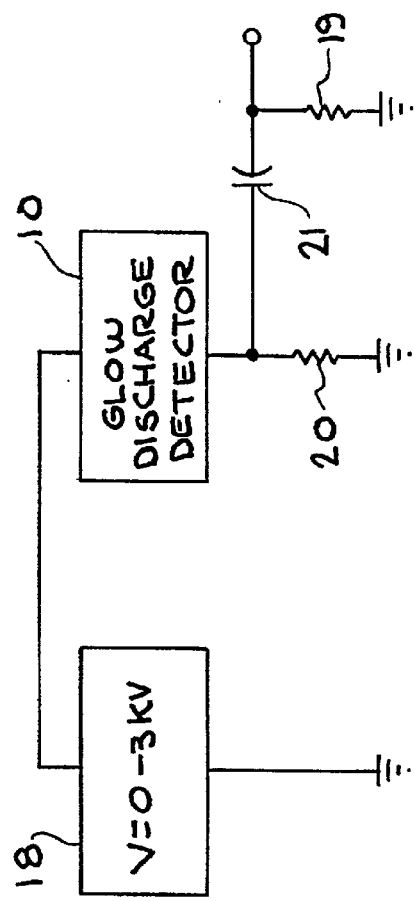
FIG. 2 schematically illustrates an embodiment of an electrical circuit for control of the glow discharge detector of FIG. 1 through a biased resistor.

The electric circuit for the glow discharge detector 10 of FIG. 1 is shown schematically in FIG. 2, and includes a power supply 18 having a voltage (V) of 0–3 KV, first resistor 19 having a resistance R=5 M ohm, and a second resistor 20 having a resistance RO=3.5 M ohm, and a capacitor 21 having a capacitance (C)=0.02 MF.

Case 1: In a helium gas with low concentration of sample gases, because of the low possibility of ionization, these sample molecules will inter-mix with the helium gas molecules and ions in the cathode dark space and causes a decrease of the value of the large electrolytic capacitance. To maintain the same value for the surface charge on the emission point, the value of the voltage drop across the cathode dark space will have to increase. By measuring this voltage drop as the sample gases pass by, one can monitor the variation of this voltage drop due to the low concentration of the sample gases. In this case, there is a negative signal.

Case 2: In a helium gas with high concentration of sample gases or sample gasses by their own, a part of the sample gases in this case will be ionized. The ionized sample molecules can increase the value of the large electrolytic capacitance in the cathode dark space. Therefore, it can lower the voltage drop across the cathode dark space. Then, in this case, there is a positive signal.

Case 3: Even in the first case where the concentration of the sample gases is quite low, there is a possibility that the excited helium molecules can interact with the sample molecules and make them ionized. In this case, there also existed the possibility that one will get a positive signal.

Figure 3:
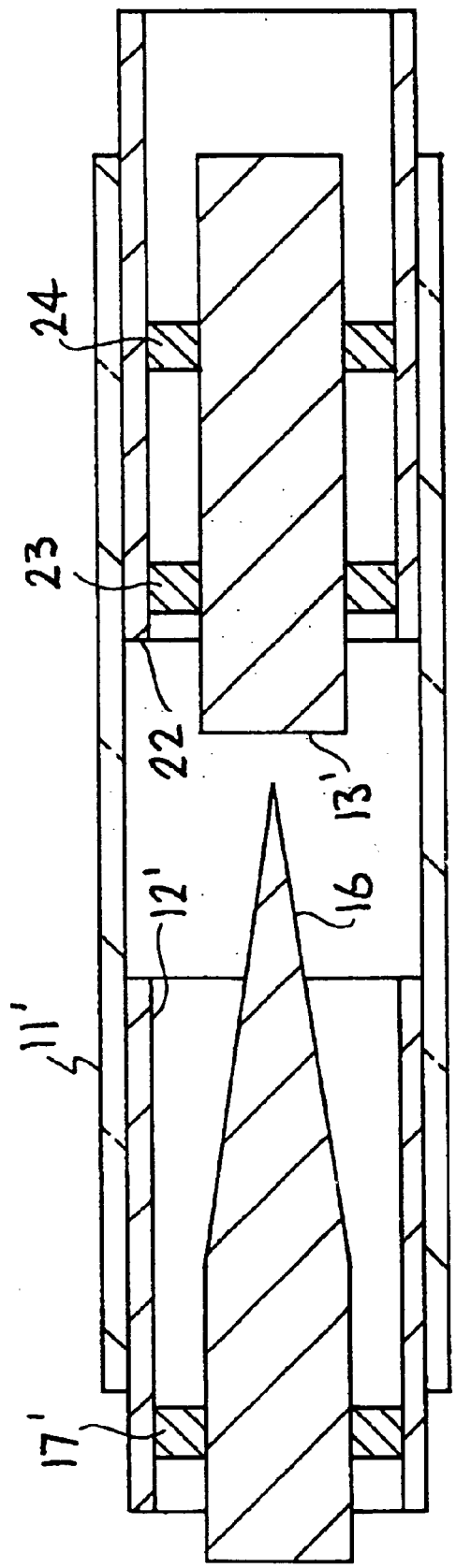
FIG. 3 schematically illustrates a more stable embodiment of the glow discharge detector of FIG. 1.

FIG. 3 illustrates an embodiment of the improved or more stable glow discharge detector of the present invention. The FIG. 3 embodiment differs from the FIG. 1 embodiment by replacing the hollow tube anode 13 of FIG. 1 with a solid rod anode made of refractory metals with low work functions such as, tungsten, molybdenum, uranium, platinum and etc., or normal metals like copper or gold which would not be poisoned by oxygen to achieve a more stable system for easier alignment. Components of FIG. 3 corresponding to those of FIG. 1 are given similar reference numerals. As seen in FIG. 3, the solid rod anode 13 is supported within a tube 22 that may be made of stainless steel, copper or preferably other refractory metals with low work functions such as, tungsten, molybdenum, uranium and etc., or normal metals like copper or gold which would not be poisoned by oxygen, via a pair of pinched areas 23 and 24 of tube 22, similar to pinched area 17 of FIG. 1, or by separate support members, so as to provide minimal blockage of gas flow through the detector. The electrical circuit of FIG. 2 can be used for FIG. 3 also.

With the glow discharge detector of the present invention: 1) there are both positive and negative signals due to the discharge or re-charge of the large electrolyte capacitance in the dark space, the signals in the above-referenced micro detectors being unidirectional; 2) the glow region is not important, which is contrary to the prior known mirco detectors, since the cathode dark space is only microns in thickness; 3) contrary to the above-referenced micro detectors, the gas flow rate of the present detector has a minimum effect to the detection sensitivity, it being only important in stabilizing the glow discharge; 4) since all glow discharges have cathode dark spaces, the glow discharge used in the present detector can be in any shape or size as the instrument designer desires, as long as, the sample gases can flow through or by the dark space of the glow discharge; and 5) helium gas as a carrier gas is important for the present detector, but not the above-references prior micro detectors.

It has thus been shown that the present invention provides a high sensitive device for trace element (impurity) detection, using glow discharge. The detector utilizes a DC, constant wave glow discharge controlled through a biased resistor, and a floating pseudo-electrode which forms a probe by which the large variation of electron density due to trace amount of impurities can be directly measured. The stable glow discharge detector is particularly applicable for use with portable (hand-held) gas chromatographs where the sample sizes are in the nano or sub-micro-liters size.

While a particular embodiment of the invention has been illustrated and described, and particular parameters have been set forth to exemplify and explain the principles of the invention, such are not intended to be limiting. Modifications and changes may become apparent to those skilled in the art, and it is intended that the invention be limited only by the scope of the appended claims.

What is claimed is:

1. A glow discharge detector, comprising:
   a first annular member,
   a pair of annular members mounted in spaced relation in said first annular member,
   a member having a tapering end mounted in one of said pair of annular members, and
   a solid rod having a flat end mounted in another of said pair of annular members with the flat end located closely adjacent the tapering end.

2. The detector of claim 1, wherein said first annular member comprises a glass tube.

3. The detector of claim 2, wherein said pair of annular members comprise a pair of stainless steel tubes.

4. The detector of claim 3, wherein each of said member having a tapering end and said solid rod is composed of tungsten.

5. The detector of claim 1, wherein said tapering end of said member is tapered to a point, and wherein said point is located closely adjacent to the flat end of said solid rod.

6. The detector of claim 1, additionally including an electrical circuit including a power supply, a capacitor, and a plurality of resistors.

7. The detector of claim 6, wherein said capacitor is electrically connected intermediate a pair of resistors.

8. The detector of claim 7, wherein said pair of resistors are each of a different size.

9. The glow discharge detector of claim 1, wherein said detector is controlled through a biased resistor.

10. The glow discharge detector of claim 1, wherein said member having a tapered end and said solid rod are each mounted coaxially in said first annular member.

11. The glow discharge detector of claim 1, wherein said member having a tapered end and said solid rod are mounted coaxially in said pair of annular members.

12. The glow discharge detector of claim 1, wherein said member having a tapered end and said solid rod are mounted in said pair of annular members so as to partially extend therefrom.

13. The glow discharge detector of claim 1, wherein said pair of annular members are only partially located within said first annular member.

14. In a hand-held gas chromatograph, the improvement comprising:
   a direct current, constant wave glow discharge detector,
   said detector including a solid rod anode having a flat end and
   said detector including a member having a pointed end located closely adjacent the flat end of the solid rod anode, said pointed end defining a probe whereby variations of electron density due to trace amounts of impurities in a carrier gas of the gas chromatograph can be directly measured.

15. The improvement of claim 14, wherein the constant wave glow discharge of the detector is controlled through a biased resistor.

16. The improvement of claim 14, wherein said glow discharge detector includes:

an outer annular tube composed of glass, a pair of annular tubes mounted in spaced relation in said outer annular tube and composed of stainless steel, said probe being mounted in one of said spaced pair of annular tubes, with the pointed end thereof being located closely adjacent another of said pair of annular tubes, and said pointed end member being composed of tungsten, and said solid rod anode being mounted in said another of said pair of annular tubes.

17. The improvement of claim 16, wherein said member with the pointed end is mounted in said one of said pair of annular tubes by at least one pinched area in said one of said pair of annular tubes.

18. The improvement of claim 17, wherein said member with the pointed end, said solid rod anode, and said pair of annular tubes are each mounted coaxially in said outer annular tube.

19. The improvement of claim 17, wherein said pair of annular tubes are only partially located within said outer annular tube.

20. The improvement of claim 17, wherein, said member with the pointed end and said solid rod anode are composed of refractory metals with low work functions selected from the group consisting of tungsten, molybdenum, and urananium or metals composed of copper or gold which would not be poisoned by oxygen.

* * * * *